Figure 3:
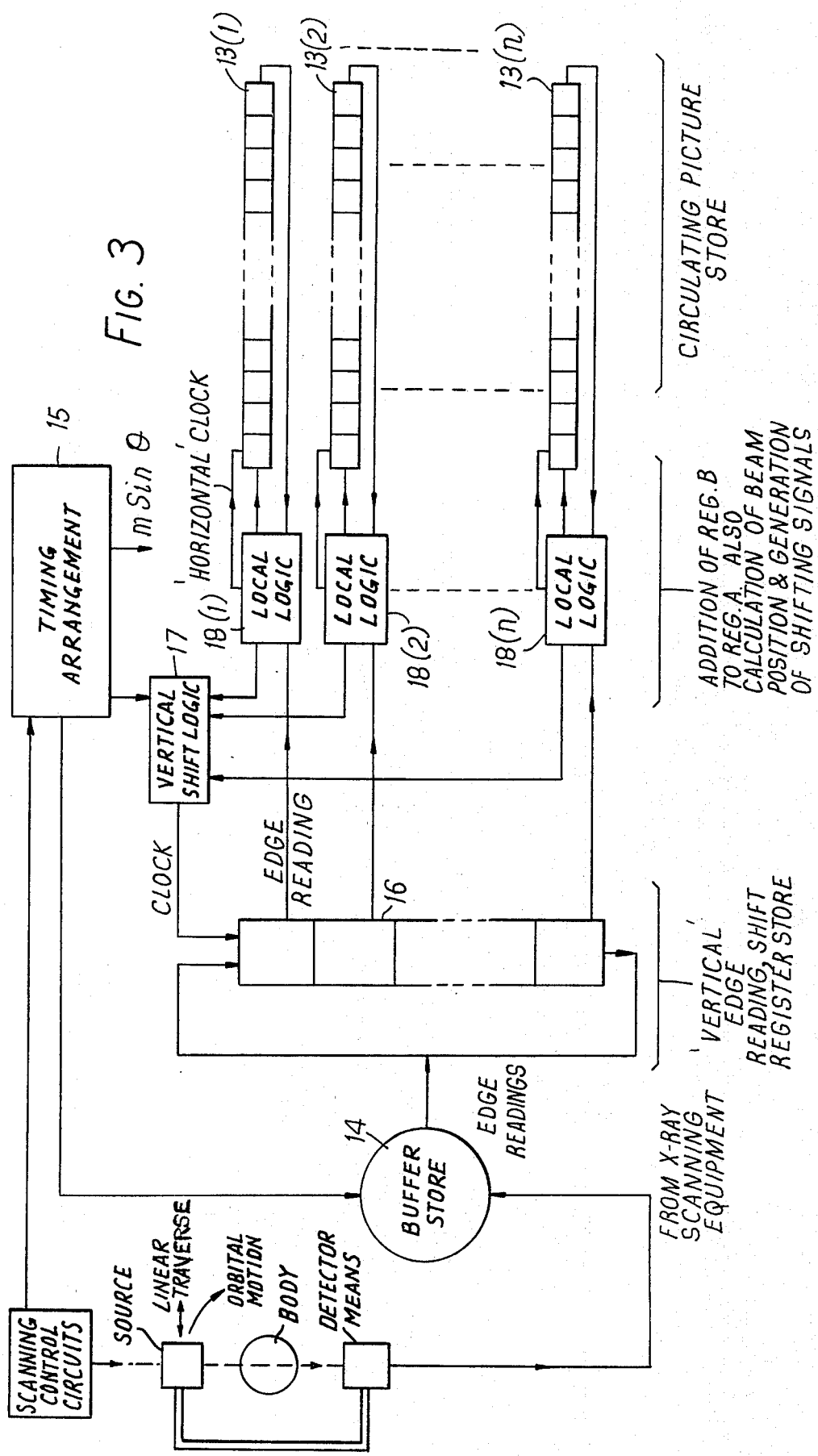

United States Patent [19]
Hounsfield et al.

[11] 3,940,599
[45] Feb. 24, 1976

[54] DATA PROCESSING ARRANGEMENTS

[75] Inventors: Godfrey Newbold Hounsfield, Newark; Paul Anthony Beaven, Langley; Brian Herbert Lill, Flackwell Heath, all of England

[73] Assignee: E M I Limited, Hayes, England

[22] Filed: May 23, 1974

[21] Appl. No.: 472,872

[30] Foreign Application Priority Data
May 23, 1973 United Kingdom................ 24773/73

[52] U.S. Cl............................ 235/151.3; 235/181
[51] Int. Cl.² ........................................ G06F 15/34
[58] Field of Search ...... 235/151.3, 181; 340/146.2; 444/1

[56] References Cited
UNITED STATES PATENTS
3,717,756 2/1973 Stitt .................................. 235/181

Primary Examiner—R. Stephen Dildine, Jr.
Attorney, Agent, or Firm—Fleit & Jacobson

[57] ABSTRACT

A data processing arrangement includes first storage means having storage locations arranged in a plurality of rows and second storage means comprising a single column of locations, one location being provided in said second storage means for each row of the locations in said first storage means. In order that the data stored in the two storage means can be correlated such that a combination of the data held in various locations of the first storage means can be compared with a corresponding value in a location of said second storage means, there is provided means for shifting the data held in the first and second storage means, at individually controllable rates, along said rows and said column respectively.

8 Claims, 6 Drawing Figures

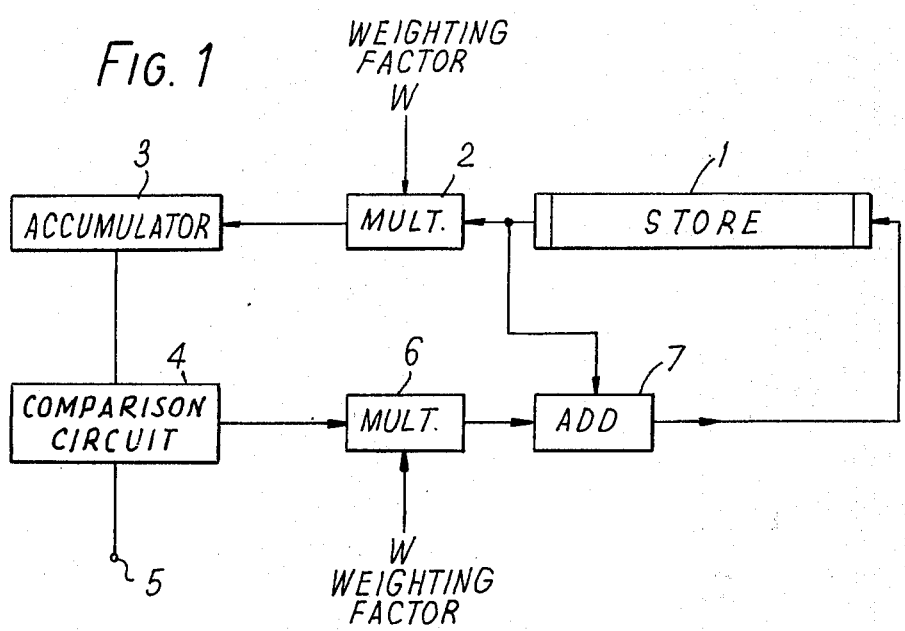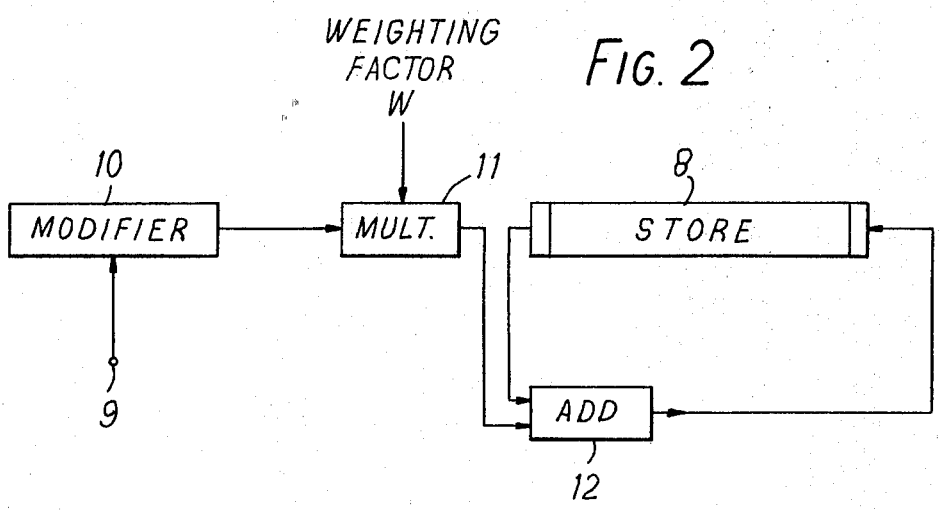

DATA PROCESSING ARRANGEMENTS

The present invention relates to data processing apparatus and methods and it relates more particularly to apparatus and methods involving the subjection of stored information to a series of processing stages, wherein the various stages of the processing require the stored information to be retrieved from the store in respective, different sequences. In accordance with this invention there is provided a data processing arrangement including:
 a. first storage means for storing electrical signals indicative of the value of a function at each of a plurality of different spatial locations of a region,
 b. second storage means for storing electrical signals indicative of the overall value of the function over linear combinations of some of said locations,
 c. menas for correlating the information stored in said first and second storage means, to update the signals stored in said first storage means which relate to the locations of said combinations, comprising
  i. means for shifting the information stored in each of said storage means at respective rates,
  ii. means for controlling said rates in dependence upon the disposition of said linear combinations of elements with respect to said region and
  iii. means for combining some of the information stored in said first and second storage means, and
 d. means for replacing the signals in said second storage means with other signals indicative of a further overall value of the function over further linear combinations of some of said locations so that the signals in said first storage means may be further updated.

Each edge reading is compared with a respective estimate of the total absorption which would have been suffered by the respective ray had the stored values for the elements inter-sected by the ray been correct, so as to derive an error signal (dependent upon the disconformity between the true edge reading and the estimate) which is distributed amongst the relevant storage locations so as to up-date the information held in the store.

It will be appreciated that, for each set of rays, all the storage locations of the store may have to be addressed but that the order in which the locations are addressed will be different for the different sets of rays because each set of rays is directed through the notional matrix of elements at a respective angle or mean angle relative thereto.

It will also be appreciated that, in general, the axis of a ray will not pass exactly through the centre of each element along its path. Typically the ray will overlap parts of elements and it is necessary to weight the stored values, used in the reconstruction of said estimates and the amounts of error signal distributed among the various storage locations, accordingly.

In accordance with this invention there is provided a data processing arrangement including first storage means for storing electrical signals indicative of the value of a function at each of a plurality of different spatial locations of a region, second storage means for storing electrical signals indicative of the overall value of the function over linear combinations of some of said locations, and means for correlating the information stored in said first and second storage means, to up-date the signals stored in said first storage means which relate to the locations of said combinations, comprising means for shifting the information stored in each of said storage means at respective rates and means for controlling said rates in dependence upon the disposition of said linear combinations of elements with respect to said region.

The present invention also encompasses methods of processing data so as to produce variable correlations of input and stored signals.

Figure 4:
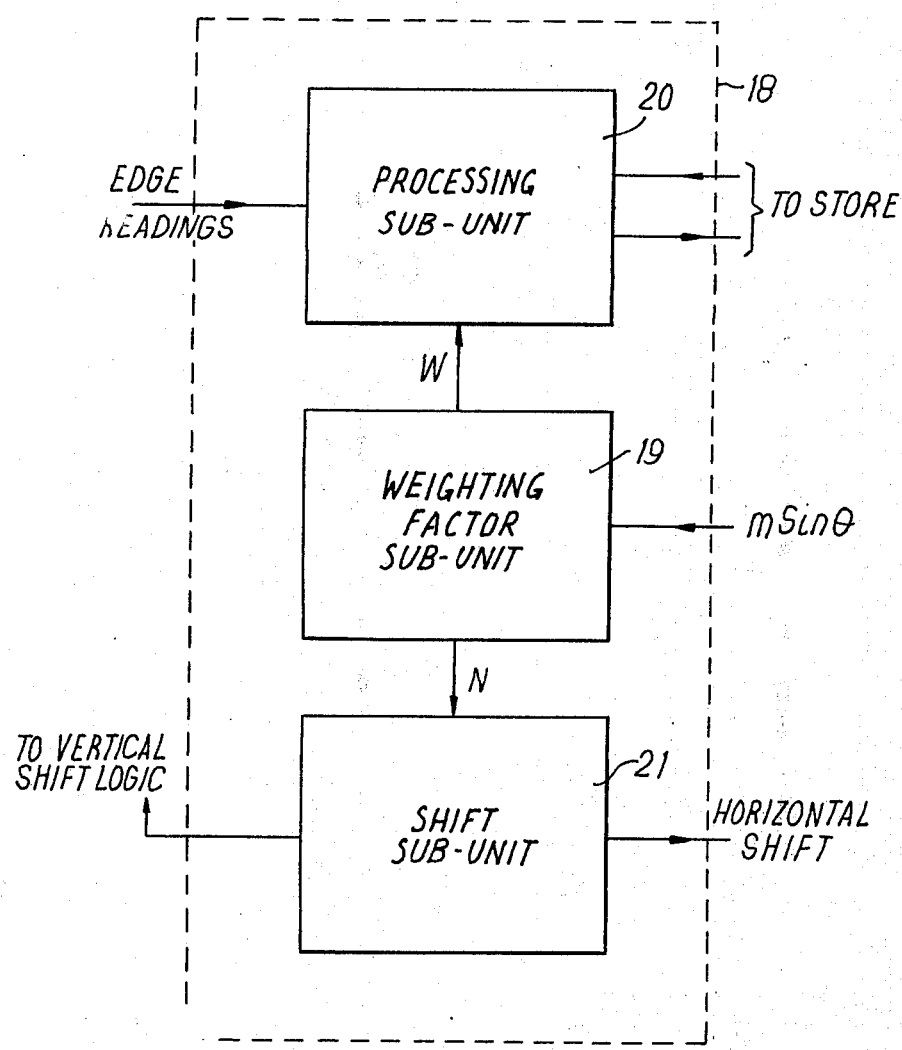
Figure 5:
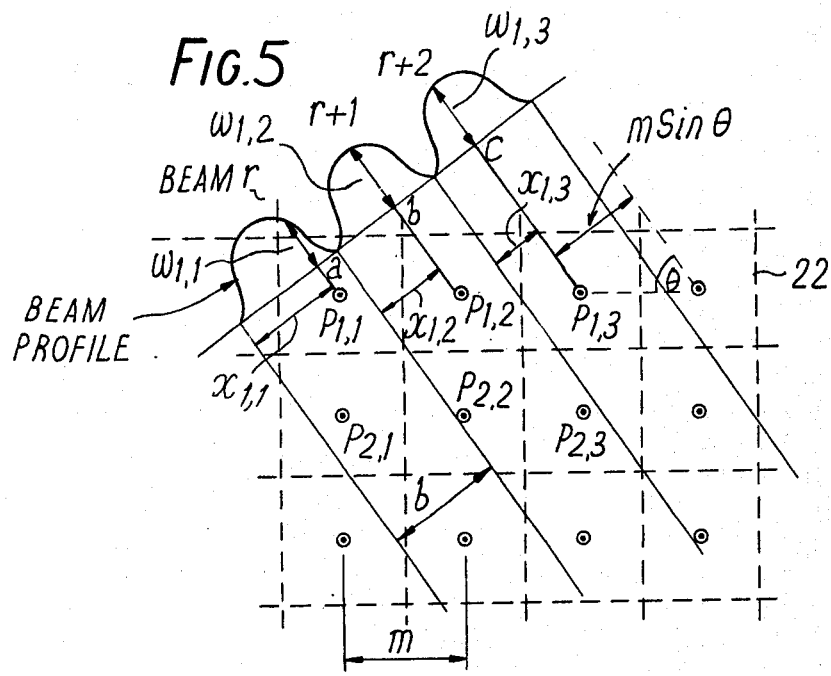
Figure 6:
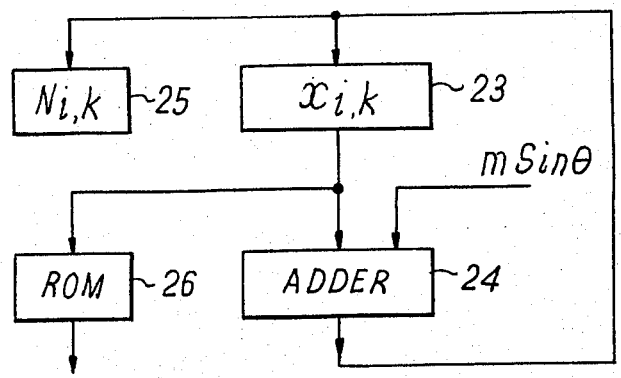

In order that the invention may be clearly understood and readily carried into effect, the following description of an arrangement in accordance with one example of the invention, together with details of associated arrangements for use in a particular embodiment of the invention, is provided by way of example only. Reference will be made to the accompanying drawings of which:

FIGS. 1 and 2 represent, in block diagrammatic form, respective processing arrangements in which the invention may be employed, FIG. 3 represents an arrangement in accordance with one example of the invention, FIG. 4 shows, in block diagrammatic form, a logic unit suitable for use in the arrangement represented in FIG. 3, FIG. 5 shows, schematically, the relationship between part of a set of rays used for investigating a body and a two-dimensional array of elements notionally delineated in said body, and FIG. 6 shows, in block diagrammatic form, a logical sub-unit suitable for incorporation in the unit shown in FIG. 4.

Referring now to the drawings, FIG. 1 shows, in block diagrammatic form, a processing arrangement which can be used to put into effect the radiographic technique described and claimed in the aforesaid Patent Specification.

A coefficient store 1 is provided with a storage location for each element of the notional matrix referred to previously. It will be assumed that each location of the store 1 holds an estimate of the absorption (or transmission) coefficient, with respect to the radiation used for investigation, of the appropriate element of the matrix, though the estimate may be zero or some finite, uniform value at the beginning of an estimation process.

When an edge reading, indicative of the actual absorption suffered by a ray on traversing a given path through the body (and thus through the matrix) is derived directly from a radiation detector, it is known, from the disposition of the ray with respect to the body, that the particular path of the ray in question intersects, to some extent, each element of a given combination of the elements of the matrix. The store 1 is then addressed, by means not shown, so as to derive therefrom the stored estimates respective to each of the elements of said combination. The estimated values derived from the store 1 are passed to a multiplying circuit 2 wherein each value is multiplied by a weighting factor which is determined by the amount of overlap between the ray path and the respective element of the matrix. The weighting factors are held in a second store which is not shown. The appropriately weighted estimated values are then summed in an accumulating unit 3 and fed to a comparison circuit 4 which also receives the actual edge reading relating to the ray in question (i.e. information derived directly from the elements of the matrix) from a terminal 5.

If the stored values were correct, the comparison would yield an error signal of zero, but in general this will not be the case and the comparison circuit 4 provides an error signal which is indicative of the degree of discrepancy between the sum of the estimated values and the detected value of absorption. A correction signal is then derived from said error signal and the correction signal is distributed among the storage locations in store 1 for all the elements in the combination without favour, apart from utilising the weighting factors again to ensure that over-correction does not occur as could happen if the full correction signal were applied to a location appropriate to an element only partly intersected by the ray. The second weighting factor operation is carried out in a multiplying circuit 6 and the output information from circuit 6 is added, with appropriate timing, to the corresponding information held in the store 1 by means of an adding circuit 7. The output information from adder 7 is fed into the appropriate storage locations of store 1.

It will be appreciated that the above-described operation is carried out for all rays in a set and for all sets of rays. The operation is one of successive approximations, i.e. an error correcting process, and it is usually necessary to repeat the operation for each ray at least once, in order that the absorption or transmission coefficients of the elements of the matrix can be determined with a substantial degree of accuracy.

FIG. 2 shows, in block diagrammatic form, an alternative processing arrangement to that shown in FIG. 1, which is a socalled "one-shot" arrangement — i.e. no repetition of the operation is required.

In the alternative arrangement, a coefficient store 8 is provided which is similar to the store 1 in the FIG. 1 arrangement. The edge readings relating to the absorption suffered by individual rays on their passage through the body are applied to a terminal 9 and modified as described in U.S. patent application Ser. No. 462,104 corresponding to British patent application Ser. No. 19528/73 in a modifier circuit 10, the operation of which is more fully explained in the aforementioned patent application. In essence, each edge reading is modified by the addition thereto of the sum of the products of respective modifying factors and other edge readings from the same set, the modifying factors being dependent upon the distance between the rays appropriate to the edge readings. An amount dependent upon the modified edge reading for a ray is distributed to each of the elements intersected by that ray, subject to multiplication by a weighting factor in a circuit 11 for the same reason as was discussed above in relation to the FIG. 1 arrangement. The distribution is effected by adding, with appropriate timing, the weighted amount to the values already stored in the appropriate locations of the store 8.

The operation of either of the arrangements described thus far poses difficulties of access to the stores (1 or 8 as the case may be) since it is necessary to derive information from (or insert information into) different combinations of locations of the store in dependence upon the orientation with respect to the aforementioned matrix of the various rays.

Thus two difficulties arise:

a. that of determining which elements are intersected by the various rays, and b. that since the entire store has to be interrogated for every set of rays, the interrogation must be sufficiently rapid to enable a result to be produced within the order of a few minutes.

It is an object of this invention to provide a data processing arrangement which can cope with the above difficulties.

FIG. 3 represents, in block diagrammatic form, an arrangement in accordance with one example of the invention, in combination with a scanning apparatus for scanning a source of X-radiation and a detector means relative to a body being examined. As described in U.S. Pat. No. 1,283,915, the scanning can consist of interrelated linear traverses and orbital motions, which are effected under the influence of scanning control circuits. In FIG. 3, the store corresponding to 1 (FIG. 1) or 8 (FIG. 2) comprises a bank of recirculating shift registers 13(1), 13(2)...13(n) — one register for each "row" of elements in the notional matrix. Each register 13 has $n$ storage locations (one for each "column" of the matrix) each capable of storing a word having sufficient bits of information to provide the required accuracy. Typically 10 to 16 bits are required. Therefore, connections for the passage of words which are shown diagrammatically as single connections in the drawings are in fact multiple parallel connections, as well known to those skilled in the art. The edge readings, derived from the scanning apparatus, are applied to an intermediate (buffer) storage arrangement, in this example a magnetic disc 14, and are applied from the buffer store under the control of clock pulses from a timing arrangement 15 to a further shift register 16 which has $n$ storage locations. The register 16 is capable of bi-directional shift and also has parallel accessing facilities. The shifting operation of register 16 is controlled by means of a vertical shift logic circuit 17, which is itself controlled by means of clock pulses from the arrangement 15. The shifting operation of each of the registers 13 is controlled by means of a respective local logic circuit 18(1), 18(2)...18(n); each local logic circuit 18 having an output information line connected to the circuit 17. Each circuit 18 receives an input of m sin $\theta$, which will be defined hereinafter, from the timing arrangement 15.

By suitably controlling the shifting rates of information held in the "horizontal" stores 13 and the "vertical" store 16, the movement of information into the store 16 can be correlated with a selected combination of the information held in the stores 13, thus simulating the path of a given ray through the aforementioned notional matrix. The simplest case occurs when the information in store 16 is held stationary and the stores 13 are all synchronously pulsed. This causes the information held in all locations of a store 13 — say the store 13(1) — to be correlated with the information held in a single bank of the store 16, thus simulating a ray passing directly through the appropriate row of elements of the notional matrix.

For an arbitrary angle $\theta$ between a ray and a matrix row, the arrangement in accordance with this example of the invention requires in theory that the following relationship be maintained:-

$$CV/CH = \tan \theta.$$

where $CV$ represents the shift rate applied to the "vertical" store 16 and $CH$ represents the average shift rate applied to the "horizontal" stores 13.

In practice, however, the fact that a finite matrix of elements is being investigated imposes a spatial quantisation so that the effective relative movement achieved by the shifts applied to stores 13 and to store 16 comprises a discontinuous function. Such a discontinuous function can be simulated by causing the logic circuits 17 and 18 to operate in an appropriate manner.

FIG. 4 shows, in block diagrammatic form, the construction of one of the logic circuits 18 depicted in FIG. 3. The circuit of FIG. 4, shown generally within the dashed rectangle 18, includes three sub-units 19, 20 and 21. Sub-unit 19 receives the aforementioned input signal $m \sin \theta$ from the timing arrangement 15 and is effective to provide an output signal W to the sub-unit 20. The signal W is the aforementioned weighting factor and is determined by calculation of the degree of overlap between a ray and the successive elements along its path; W taking a respective value for each such overlap. The sub-unit 20 receives the edge readings from the vertical store 16 (FIG. 3) and communicates with a respective horizontal store 13 and comprises, for example either the components 2 to 7 shown in FIG. 1 or the components 9 to 12 shown in FIG. 2.

The shifting of the information held in the horizontal store 13 is controlled by means of the sub-unit 21 which receives input information derived from the operation of sub-unit 19; the signal fed from sub-unit 19 to sub-unit 21 being designated N, since it represents a so-called "next ray" signal which will be described hereinafter. The sub-unit 21 is connected to the logic unit 17 which controls the shift of information through the store 16 so that the logic units 18, which operate respective ones of the horizontal stores 13, also contribute to the operation of the unit 17.

Referring now to FIG. 5, it is assumed for simplicity of description that the disposition of rays in a set is such that adjacent rays just touch but do not overlap. In practice, overlapping is achieved by repeating the scanning with a transverse shift of less than one beam width imparted to the rays. In FIG. 5, part of the notional matrix of elements is shown generally, in dashed outline, at 22. The centres of twelve elements constituting part of said matrix and arranged themselves in a three-by-four rectangular sub-matrix, are marked $P_{ij}$, the suffix $i$ representing the row of the sub-matrix in which the elements lies and the suffix $j$ representing the appropriate column of the sub-matrix.

For simplicity of description, it will be assumed hereinafter that all the matter of a given element in the sub matrix is located at its centre $P_{ij}$, so that points rather than square elements can be considered. Moreover, the cross-sectional energy distribution of the rays is assumed to be of the general form shown in FIG. 5.

From FIG. 5 it will be observed that the point P11 is intersected by the r'th ray of a set directed through the matrix 22 at an angle $\theta$ to the horizontal rows thereof. The disposition of the ray to the point is such that the energy passed through point P11 is represented by a point $(a)$ on the aforementioned energy distribution curve for the ray. Similarly the energy passed through point P12 is represented by a point $(b)$ on the corresponding curve for ray $(r+1)$ of the set and the energy passed through point P13 is represented by a point $(c)$ on the curve for ray $(r+2)$ of the set. If the distance of P11 from the left-hand edge of the r'th ray (measured perpendicularly to the extent of the ray and in the plane of the matrix) is represented as shown by $x_{11}$, and given that $x_{11}$ is known, the corresponding distances $x_{12}$, $x_{13}$ etc. can be provided by the following relationship:

$$x_{1(k+k)} = x_{1k} + n \sin \theta / _{mod\, b}$$

where $b$ represents the cross-sectional width of each ray, $m$ is the spacing between centres of adjacent elements in the same row of the matrix, and $\theta$ represents, as already defined, the angle between the rays of a set and the horizontal rows of the matrix.

The significance of the value $m \sin \theta$ referred to earlier can be easily seen from FIG. 5, this value representing the spacing between the centres of adjacent elements in the same row of the matrix measured in the same direction as the values $x_{11}$ etc.

FIG. 6 shows, in more detail though still in block diagrammatic form, a typical construction for the sub-unit 19 referred to during the description of FIG. 4. This sub-unit receives only the signal $m \sin \theta$ as input information and from this it is arranged to generate the "next beam" signal N, the distance $x_{ij}$ and the corresponding weighting factor W, utilising the relationship for $x_{1(t+k)}$ set out above. The value $x_{11}$ is assumed to be known and held initially in a unit 23. When a value of $m \sin \theta$ is received from the arrangement 15, it is applied to an adder unit 24 wherein it is summed with the value for $x_{11}$, the sum being decremented by the fixed amount $b$, and the output of the adder unit 24 is applied to the unit 23, which then holds the up-dated value $x_{12}$, and also to a unit 25 for generating the signal N, which in this example is either "1" or "0" as will be described hereinafter. The unit 25 is arranged, using known techniques, to produce a signal corresponding to $N = 1$ if $(x_{1k} + m \sin \theta) \geq b$ and to produce a signal corresponding to $N = 0$, if $(x_{1k} + m \sin \theta) < b$.

The value currently held in the unit 23 is also applied to a further unit 26 which correlates the value with the (fixed) energy distribution curve of the rays to generate the weighting factor W for the particular intersection of a ray and an element.

When N takes the value 0, this indicates that the element giving rise to the value $x_1(k+1)$ lies in the same ray as the element giving rise to the value $x_{1k}$ whereas when N takes the value 1, this indicates that the two elements lie in adjacent rays. The situation in which N takes the value 1 for all rows of the matrix (i.e. the sub-unit 19 of the unit 18 associated with each of the horizontal stores 13 gives an output of 1) is used by logic unit 17 to generate a shift pulse for the vertical store 16. When this condition occurs, it indicates that all the elements whose storage locations are being accessed at that time are in an adjacent beam, and a shift of the information in the vertical store 16 is required to re-align the storage locations of the stores 13 and 16.

It is convenient, from a practical point of view, for $b$ to take the value unity. In this case, the adder unit 24 can be divided into integer and positive fractional parts, where the integer part gives the signal N and the fractional part provides the corresponding value of $x$. Each time the next element in a given row of the notional matrix is to be considered, the quantity $m \sin \theta$ is added by a suitably operated gate (not shown) to the unit 24. It will be appreciated that the value of $m \sin \theta$ is a constant for a given set of rays.

In a practical embodiment of this example of the invention the horizontal stores 13 are only capable of shifting the information held therein in one direction. The vertical store 16, however, has to be capable of bi-directional shifts. The "vertical" shift is upward or downward as determined by the angle $\theta$.

In an alternative arrangement of the stores 13 and 16, the "horizontal" stores are extended to store the values for l adjacent rows of elements; l taking the value four in this example. This arrangement permits a reduction by a factor of l in the number of local logic circuits 18 to be achieved at the expense of having larger (though fewer) horizontal stores. The increase in size of the horizontal stores is of little significance in itself from an economic point of view, but the speed of operation of the arrangement is, of course, reduced. In effect, this arrangement exchanges cost of local logic units (18) for speed of operation.

The technique for providing horizontal and vertical shifts is substantially the same as with the previously described embodiment, except that the horizontal and vertical stores are each addressed 1 times instead of one for each set of rays.

Although the invention has been described in terms of the use of parallel rays, sets of mutually divergent rays can alternatively be used if desired. Each set of rays may be tilted through an angle, corresponding to the inter-ray angle of a set, relative to the preceding set of rays so as to establish different sets of parallel rays.

Although the invention has been described with reference to the use of shift register stores for the edge readings and the coefficients of the elements of the body, this need not necessarily be the case and the stores could comprise instead random access stores in a digital computer which is arranged to carry out the various processing steps.

What we claim is:

1. A data processing arrangement including
   a. first storage means for storing electrical signals indicative of the value of a function at each of a plurality of different spatial locations of a region,
   b. second storage means for storing electrical signals indicative of the overall value of the function over linear combinations of some of said locations,
   c. means for correlating the information stored in said first and second storage means, to update the signals stored in said first storage means which relate to the locations of said combinations, comprising
      i. means for shifting the information stored in each of said storage means at respective rates,
      ii. means for controlling said rates in dependence upon the disposition of said linear combinations of elements with respect to said region and
      iii. means for combining some of the information stored in said first and second storage means, and
   d. means for replacing the signals in said second storage means with other signals indicative of a further overall value of the function over further linear combinations of some of said locations so that the signals in said first storage means may be further updated.

2. A scanning apparatus for investigating a body by means of penetrating radiation such as X- or γ- radiation including a data processing arrangement including
   a. first storage means for storing electrical signals indicative of the value of a function at each of a plurality of different spatial locations of a region,
   b. second storage means for storing electrical signals indicative of the overall value of the function over linear combinations of some of said locations,
   c. means for correlating the information stored in said first and second storage means, to update the signals stored in said first storage means which relate to the locations of said combinations, comprising
      i. means for shifting the information stored in each of said storage means at respective rates,
      ii. means for controlling said rates in dependence upon the disposition of said linear combinations of elements with respect to said region and
      iii. means for combining some of the information stored in said first and second storage means, and
   d. means for replacing the signals in said second storage means with other signals indicative of a further overall value of the function over further linear combinations of some of said locations so that the signals in said first storage means may be further updated.

3. A scanning apparatus according to claim 2 wherein said scanning apparatus includes a source of said radiation, means for directing a plurality of co-planar rays of said radiation through a substantially planar slice of said body, said slice corresponding to said region, such that each ray defines a respective linear combination of said locations, and detecting means arranged to receive radiation emergent from said body along each of said rays and to provide an electrical output signal for each ray indicative of the absorption of said radiation disposed along the combination intersected by said ray.

4. A scanning apparatus according to claim 2 wherein said data processing arrangement includes, in said first storage means, a storage compartment respective to each of said locations, the locations being arranged in rows and columns in said region, and the compartments being likewise arranged in corresponding rows and columns, shift means being provided for moving the information held in said first storage means, at a controllable rate, in the direction of said rows only.

5. A scanning apparatus according to claim 4 wherein said second storage means comprises a bi-directional shift register arranged to receive the data provided by said scanning apparatus, further shift means being provided for moving said data through said register, at a controllable rate, in the direction of the columns of information held in said first storage means.

6. A scanning apparatus according to claim 5 wherein said means for correlating comprises a respective local logic circuit associated with each row of compartments in said first storage means, said shift register having a respective location corresponding to each of said rows, and comprising
   a. a processing sub-unit arranged to receive information from both said first and second storage means, to correlate said information and to up-date the information held in said first storage means in accordance with said correlation,
   b. a weighting factor sub-unit for receiving signals from said timing circuit and for evaluating weighting factor signals used in said correlation, and
   c. a shift sub-unit arranged to communicate with said weighting factor sub-unit and to provide shifting information for said first and second storage means.

7. A scanning apparatus according to claim 6 wherein said first mentioned shift means is caused to operate under the control of a timing circuit which is linked to the operations of said scanning apparatus.

8. A scanning apparatus according to claim 7 wherein said further shift means is caused to operate under the control of said timing circuit and also said first mentioned shift means.

* * * * *

UNITED STATES PATENT OFFICE
CERTIFICATE OF CORRECTION

PATENT NO. : 3,940,599

DATED : February 24, 1976

Page 1 of 2

INVENTOR(S) : GODFREY NEWBOLD HOUNSFIELD ET AL

It is certified that error appears in the above-identified patent and that said Letters Patent are hereby corrected as shown below:

Column 1, lines 10-36, cancel "In accordance . . . further updated." and insert the following:

--Such processing is involved, for example, in the radiographic technique described in our British Patent Specification No. 1,283,915, wherein a store is provided having respective storage locations for amounts representing the absorption (or transmission) coefficients of the elements of a two-dimensional matrix notionally delineated in a planar slice of a body which is being examined by means of radiation such as X- or $\gamma$-radiation. The radiation is directed through the body along a plurality of similar sets of rays, each set being directed through the body at a respective angle, or mean angle, with respect to said matrix and in the plane thereof. The radiation emergent from the body along each ray is detected and manipulated to produce signals called edge readings which are indicative of the amount of radiation absorbed by the elements of the body disposed along each of said rays.--

Column 1, line 61 - Column 2, line 7, cancel "data processing . . . said region." and insert the following:

--data processing arrangement including

--a. first storage means for storing electrical signals indicative of the value of a function at each of a plurality of different spatial locations of a region, --b. second storage means for storing electrical signals indicative of the overall value of the function over linear combinations of some of said locations,

UNITED STATES PATENT OFFICE
CERTIFICATE OF CORRECTION

PATENT NO. : 3,940,599
DATED : February 24, 1976
INVENTOR(S) : GODFREY NEWBOLD HOUNSFIELD ET AL It is certified that error appears in the above-identified patent and that said Letters Patent are hereby corrected as shown below:

--c. means for correlating the information stored in said first and second storage means, to update the signals stored in said first storage means which relate to the locations of said combinations, comprising i. means for shifting the information stored in each of said storage means at respective rates, ii. means for controlling said rates in dependence upon the dispostion of said linear combinations of elements with respect to said region and iii. means for combining some of the information stored in said first and second storage means, and --d. means for replacing the signals in said second storage means with other signals indicative of a further overall value of the function over further linear combinations in some of said locations so that the signals in said first storage means may be further updated.--

Signed and Sealed this twenty-ninth Day of June 1976

[SEAL]

Attest:

RUTH C. MASON
*Attesting Officer*

C. MARSHALL DANN
*Commissioner of Patents and Trademarks*